US009980701B2

United States Patent
Fearnot et al.

(10) Patent No.: US 9,980,701 B2
(45) Date of Patent: May 29, 2018

(54) RECIPROCATING INTERNAL ULTRASOUND TRANSDUCER ASSEMBLY

(71) Applicant: Muffin Incorporated, West Lafayette, IN (US)

(72) Inventors: Neal E. Fearnot, West Lafayette, IN (US); Peter S. McKinnis, West Lafayette, IN (US); Sarah Robbins, Lafayette, IN (US); Yun Zhou, West Lafayette, IN (US)

(73) Assignee: Muffin Incorporated, West Lafayette, IN (US)

( * ) Notice: Subject to any disclaimer, the term of this patent is extended or adjusted under 35 U.S.C. 154(b) by 1019 days.

(21) Appl. No.: 14/051,826

(22) Filed: Oct. 11, 2013

(65) Prior Publication Data

US 2014/0107489 A1   Apr. 17, 2014

Related U.S. Application Data

(60) Provisional application No. 61/713,135, filed on Oct. 12, 2012.

(51) Int. Cl.
*A61B 8/00* (2006.01)
*A61B 8/12* (2006.01)
*G01S 15/89* (2006.01)
*A61N 7/02* (2006.01)
*A61N 7/00* (2006.01)

(52) U.S. Cl.
CPC .............. *A61B 8/4483* (2013.01); *A61B 8/12* (2013.01); *A61B 8/445* (2013.01); *A61B 8/4461* (2013.01); *G01S 15/894* (2013.01); *A61B 8/467* (2013.01); *A61N 7/022* (2013.01); *A61N 2007/0043* (2013.01)

(58) Field of Classification Search
None
See application file for complete search history.

(56) References Cited

U.S. PATENT DOCUMENTS

| 4,421,118 A | 12/1983 | Dow et al. |
| 4,720,266 A | 1/1988 | Leonard et al. |
| 4,785,816 A | 11/1988 | Dow et al. |

(Continued)

FOREIGN PATENT DOCUMENTS

| JP | 2004/129697 | 4/2004 |
| WO | WO 20121061643 A1 | 5/2012 |

OTHER PUBLICATIONS

International Search Report and Written Opinion issued in PCT/US2013/064570, dated Jan. 24, 2014.

(Continued)

*Primary Examiner* — Katherine Fernandez
*Assistant Examiner* — Marjan Saboktakin
(74) *Attorney, Agent, or Firm* — Woodard, Emhardt, Moriarty, McNett & Henry LLP

(57) ABSTRACT

A device for endoluminal therapeutic and diagnostic ultrasound procedures includes a motor which rotates a drive shaft and ultrasound transducer. In one example, conductors attach to the transducer and extend through a hollow drive shaft. In another example, a bias member conducts electric signals and stores energy. The device includes an operational state in which the motor rotates the drive shaft alternatingly between a first direction and an opposite second direction.

21 Claims, 2 Drawing Sheets

(56) References Cited

U.S. PATENT DOCUMENTS

| | | | |
|---|---|---|---|
| 4,951,677 A * | 8/1990 | Crowley | A61B 5/6848 600/109 |
| 5,373,845 A | 12/1994 | Gardineer et al. | |
| 6,241,744 B1 | 6/2001 | Imran et al. | |
| 6,371,915 B1 | 4/2002 | Koger et al. | |
| 6,684,094 B1 | 1/2004 | Lehr et al. | |
| 8,206,307 B2 | 6/2012 | Barnard et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2006/0030797 A1 | 2/2006 | Zhou et al. | |
| 2006/0173348 A1 | 8/2006 | Wilser et al. | |
| 2007/0038114 A1 | 2/2007 | Couvillon, Jr. | |
| 2007/0149917 A1 | 6/2007 | Bennett et al. | |
| 2008/0097403 A1 | 4/2008 | Donaldson et al. | |
| 2008/0177138 A1 | 7/2008 | Courtney et al. | |
| 2008/0221506 A1 | 9/2008 | Rodriguez et al. | |
| 2008/0228081 A1 * | 9/2008 | Becker | A61B 8/12 600/459 |
| 2009/0306518 A1 | 12/2009 | Kurse et al. | |
| 2010/0036258 A1 | 2/2010 | Dietz et al. | |
| 2010/0160788 A1 | 6/2010 | Davies et al. | |
| 2010/0234736 A1 | 9/2010 | Corl | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0021926 A1 * | 1/2011 | Spencer | A61B 5/0062 600/478 |
| 2011/0071400 A1 * | 3/2011 | Hastings | A61B 8/12 600/467 |
| 2011/0071401 A1 * | 3/2011 | Hastings | A61B 8/12 600/467 |
| 2011/0196266 A1 | 8/2011 | Robertson et al. | |
| 2011/0263986 A1 * | 10/2011 | Park | A61B 8/4461 600/462 |
| 2011/0301508 A1 | 12/2011 | Sethuraman et al. | |
| 2012/0172698 A1 | 7/2012 | Teo et al. | |

OTHER PUBLICATIONS

International Search Report and Written Opinion issued in PCT/US2013/064579, dated Jan. 23, 2014.

International Search Report and Written Opinion issued in PCT/US2013/064606, dated Jan. 8, 2014.

International Search Report and Written Opinion issued in PCT/US2013/064611, dated Jan. 28, 2014.

International Search Report and Written Opinion issued in PCT/US2013/064618, dated Jan. 24, 2014.

* cited by examiner

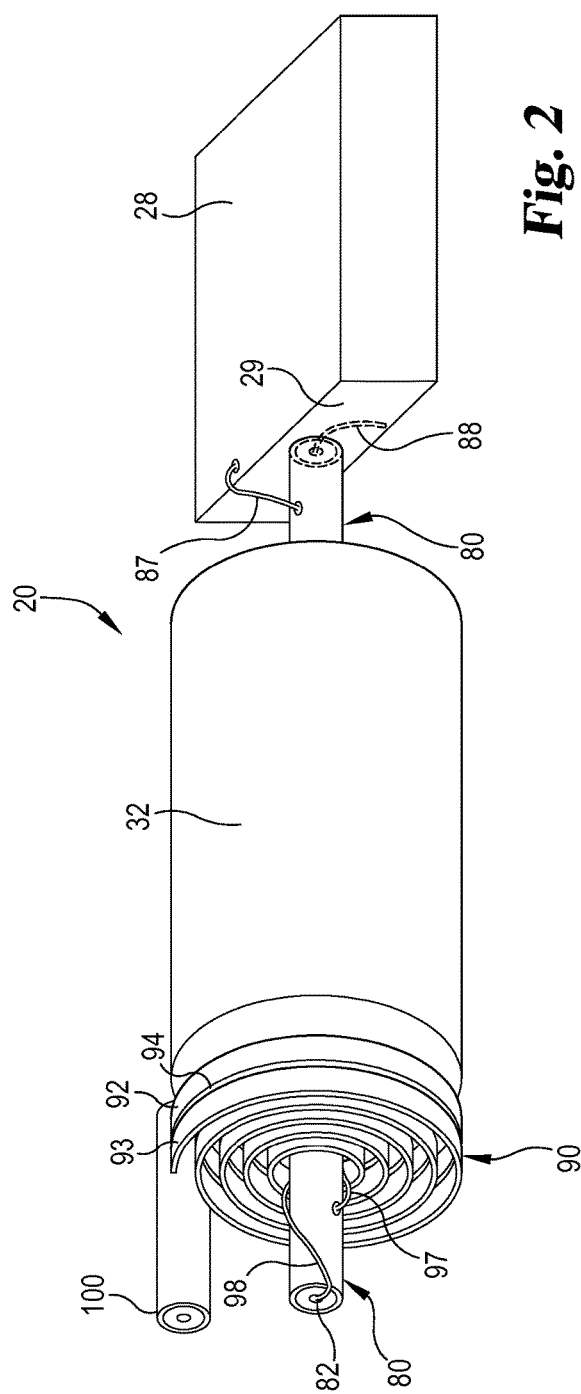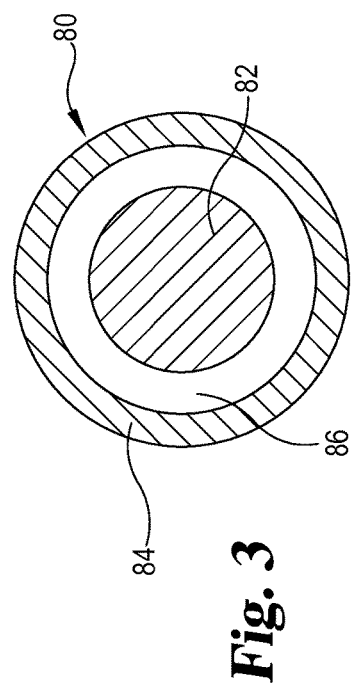

RECIPROCATING INTERNAL ULTRASOUND TRANSDUCER ASSEMBLY

CROSS-REFERENCE TO RELATED APPLICATION

This application claims the benefit of U.S. Provisional Application No. 61/713,135 filed Oct. 12, 2012, which is hereby incorporated by reference.

This disclosure concerns devices and methods for using ultrasound within the body of a patient. In particular, it concerns features that allow for efficient use in small body areas, such as within blood vessels.

BACKGROUND

Ultrasound technology has been used for therapeutic and diagnostic medical procedures, which can include providing imaging of internal portions of a body. Ultrasound procedures typically use a transducer assembly to emit and/or receive signals. In some cases, a stationary transducer assembly can view a full image area due to the particular positioning of the multiple ultrasound elements in an array. Another design includes a rotating transducer assembly having a single ultrasound element which obtains data by mechanically rotating the transducer assembly. In that case, data are obtained by the transducer assembly emitting sequential ultrasound pulses at changing rotational positions. Advantages of the single-element rotational design when compared to an array design include smaller catheter diameter, better image quality, possible higher center frequency, lower cost for the ultrasound imaging console, and less ring down artifacts (dead zone).

Single element designs can also include certain disadvantages, such as non-uniform rotational distortion (NURD). During imaging procedures including a single element design, the ultrasound element is typically rotated with a torque cable. Ultrasound pulses are emitted in an even-spaced time-sequential manner under the expectation of a uniform rotation rate of the ultrasound element. Each reflected ultrasound pulse or echo signal represents a portion or scan line of an image. An image processor assembles the data based on the assumption that the data points represent images from evenly-spaced pulses. However, it can be difficult to achieve a uniform rotation rate for the ultrasound element when using a torque cable as a driving means. The ultrasound element can be around one meter from the driving end of the torque cable. Ideally, the torque cable will have sufficient stiffness to provide uniform rotation at both ends while simultaneously allowing maneuverability. However, practically a sufficiently maneuverable torque cable creates a potential for delay in the transferring of torque from one end of the cable to the other, as the cable stores and releases elastic energy, which causes the transducer assembly to rotate at a non-uniform rate even when the rotation source rotates at a uniform rate. The non-uniform rotation rate causes the resulting images to be distorted.

Attempts to create single element designs without torque cables present further problems. Designs which include a microminiature motor positioned near a stationary transducer assembly and a rotating reflector require additional space. In addition, control wires or structural components can cross the viewing window causing a portion of an image to be blocked. Another problem is the possibility of breaking a catheter tip which includes the ultrasound transducer. Designs including a microminiature motor positioned near a rotating transducer assembly present further problems. Current commercialized designs use costly and bulky rotary transformers to connect stationary electrical wires from a console to a rotating ultrasound element. However, the rotary transformer is among the most expensive components of such imaging systems. Slip rings have disadvantages in that they take up space and can add electrical noise to the ultrasound signals.

Other problems exist in current designs. Typically, transducer assemblies are positioned in a dedicated catheter. The catheter usually shares the same utility lumen as therapeutic catheters preventing a physician from performing imaging monitoring simultaneously with or during additional procedures, such as, for example, deploying a stent or graft or performing a biopsy.

Thus, there is a need to have an ultrasound system design that could be integrated with a catheter, that is cost effective, small in size, and which produces images free from NURD artifacts and blocked viewing areas.

SUMMARY

Among other things, there are disclosed embodiments of devices for use in internal ultrasound procedures and methods for making and using them. For example, a device for internal ultrasound imaging includes a stationary motor operatively coupled with a drive shaft, wherein the drive shaft is positioned radially inward of the motor and extends substantially along a rotation axis, so that operation of the motor rotates the drive shaft about the rotation axis. A transducer configured for transmitting and/or receiving ultrasound signals is operatively coupled with the drive shaft so that the transducer rotates in response to rotation of the drive shaft. The transducer is rotatable about the rotation axis through a range which defines a viewing window extending outward from the transducer. The entire viewing window has acoustic attenuation that allows passage of imagable ultrasound signals.

A first conduction path extends from the transducer through the drive shaft, with a portion of the first conduction path including at least a first conductor integral to the drive shaft and extending through the drive shaft. The motor has an operational state in which the stationary motor rotates the drive shaft about the rotation axis alternatingly between a first rotational direction and an opposite second rotational direction. A second conduction path can extend from the transducer through the drive shaft with a portion of the second conduction path including at least a second conductor integral to the drive shaft and extending through the drive shaft. The first and second conductors can be fixedly attached within the drive shaft and rotate with the drive shaft. The drive shaft can be a coaxial cable with the first conduction path positioned concentrically relative to the second conduction path. The first and second conduction paths can have respective non-rotating control side portions that are on the control side of the motor.

The device can include a bias member having a first and second end. The first end can be fixedly attached to the drive shaft and the second end can be fixedly disposed relative to the stationary motor. The bias member can be a helical spring. The bias member can include a first bias conductor which is part of the first conduction path. The bias member can include a second bias conductor electrically insulated from the first bias conductor which is part of the second conduction path.

The drive shaft can be a hollow drive shaft defining a lumen, with the first conductor extending through the lumen. In some examples, the operational state may have the motor rotating the drive shaft at least 180 degrees in each of the first and second rotational directions, at least 360 degrees in each direction, or an arc between 270 and 360 degrees. The drive shaft can also be rotated throughout a user-defined range in each of the rotational directions.

In some examples, a fluidly sealed chamber enclosing the transducer is provided. The chamber is filled with a fluid having acoustic impedance which allows imaging therethrough. Particular examples of such fluids are saline water, mineral oil, castor oil, or mixed alcohol.

The transducer can include a backing coupled to an ultrasonic element, and the conduction path in such embodiments can pass through a portion of the backing. Particular examples have an ultrasound field defined by an orientation and rotation of the transducer. The ultrasound field can be directed away from the transducer through the viewing window in such a way that the conductors remain outside of the ultrasound field. First conduction path can have a rotating portion fixed with respect to the transducer and a non-rotating portion positioned on the control side of the motor.

In some examples, the stationary motor can be an electromagnetic motor. The device can include a catheter, in which the stationary motor and transducer are positioned within an application side portion of the catheter. In some examples, the transducer is positioned on the rotation axis.

BRIEF DESCRIPTION OF THE DRAWING

FIG. 2 is a schematic, partial perspective view of an alternative ultrasound device having a coaxial drive shaft and bias member conductor.

FIG. 3 is a cross-sectional view of the coaxial drive shaft of FIG. 2.

DESCRIPTION OF THE ILLUSTRATED EMBODIMENTS

Figure 1:
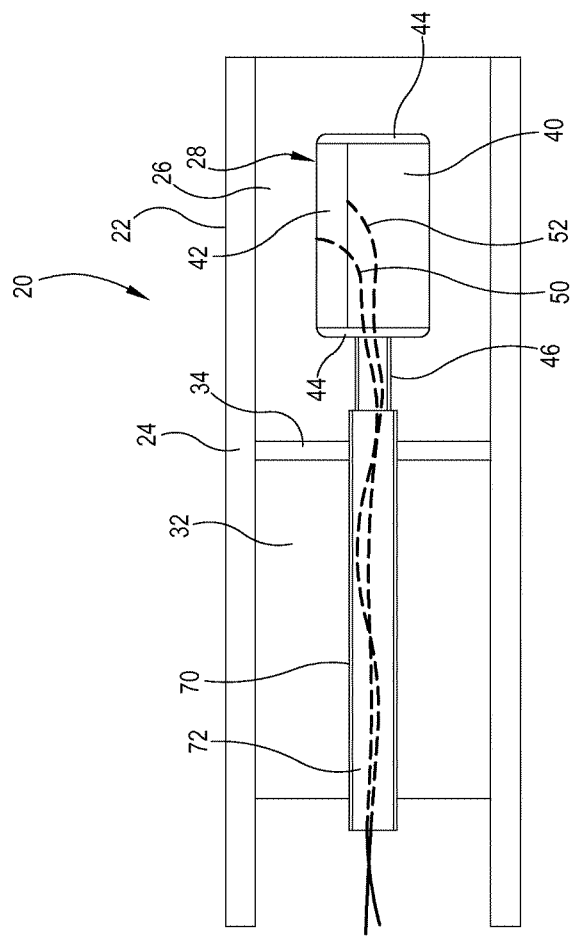
FIG. 1 is a schematic, part cross-sectional view of an ultrasound device having a hollow drive shaft.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the disclosure relates.

Referring generally to the drawings, there are shown embodiments of a device 20 suitable for endoluminal medical procedures. Device 20 can be used with a system which includes a console (not shown) and device 20. In some cases the system can be an imaging system. The ultrasound console can be a type which is generally used for medical ultrasonic imaging, e.g. generally including control devices usable by a physician and a graphic display which displays graphical images obtained during an ultrasound procedure. Device 20 can be used for obtaining images at various locations of a body such as a blood vessel, urethra, ureter, vagina, rectum, throat, ear, or through an artificial tract (or lumen) by percutaneous puncture for example. The console portion can be connected to commercially available ultrasound probes or catheters with compatible pinout, or other medical devices which are configured for endoluminal procedures. Device 20 is capable of emitting and receiving ultrasound signals and then communicating data obtained from ultrasound signals to the console. The console is configured to process the data and creates image(s) viewable on a display or other data output.

In the embodiment shown schematically in FIG. 1, device 20 includes a catheter 22 or other flexible elongated member having a wall 24 defining an internal chamber 26. Catheter 22 is sized and configured for insertion into and/or travel along bodily orifices or lumens. Positioned within chamber 26 is a transducer 28 and a motor 32 operatively coupled with transducer 28. Generally, catheter 22 provides access to a bodily location where motor 32 provides rotational motion to transducer 28. Device 20 could optionally include a motor housing (not shown) for providing structural support for motor 32 and transducer 28. Transducer 28 in conjunction with rotary motion provided by motor 32 is capable of emitting and receiving ultrasound signals in a variety of directions which are passed along data signal communication lines between transducer 28 and the ultrasound console.

Catheter 22 in the illustrated embodiment is an elongated device of plastic or other sturdy flexible material which presents a minimal barrier to the passage of ultrasound signals which is small enough that ultrasound images may be reasonably acquired through the barrier. Catheter 22 includes a control end which during use is nearest to the user and an application end which during use is nearest to the patient. The terms "control" and "application" are used throughout this description to describe these positional orientations. Wall 24 surrounds chamber 26, which is at the application end of device 20 in the illustrated embodiment. The control end of wall 24 and/or catheter 22 may extend outside of the patient during use, (or may attach to another piece that extends outside the patient), and may end in a handle or other operating portion for maneuvering catheter 22. Particular embodiments of catheter 22 or at least chamber 26 are cylindrical, and are sized for insertion into and passage through bodily orifices and lumens, such as, for example, insertion into the femoral artery and passage through it toward the heart. Wall 24 may have a port or other feature to allow injection of fluid into chamber 26, as will be discussed further below.

Catheter 22 is constructed of a material which is substantially echolucent when placed in the surrounding working environment (such as blood within a blood vessel) such that it acts as an acoustic window which allows passage of ultrasound signals with minimal reflection. Echolucency is a result of an ultrasound wave conduction path having mediums with substantially matched acoustic impedances. For example, when used within a blood vessel containing body tissues and blood, it is preferable for catheter 22 to be constructed of a material which is structurally rigid and which has acoustic impedance similar to that of body fluids such as blood. Possible materials could include, for example, a polymer material such as high density polyethylene, polymethylpentene (PMP), or acrylonitrile butadiene styrene (ABS). It has been determined that in some cases the thickness of at least the portion of catheter 22 which serves as the viewing window can be approximately ½ of the wavelength corresponding to the center frequency of the ultrasound signal.

Transducer 28 is indicated schematically in the drawings. The term "transducer" should be understood to include an assembly of two or more parts as well as a single piece. An exemplary transducer 28 includes a body or backing 40 with an ultrasound element 42 attached to one side of backing 40, and one or more clamping rings 44. Transducer 28 can include a matching layer (not shown) attached to one side of element 42. Element 42 can be a piezoelectric element which has the ability to convert electrical energy into sound waves and sound waves into electrical energy. The positioning of element 42 as indicated, adjacent to backing 40, results in a directed ultrasound beam direction. Backing 40 may be substantially opaque to or reflective of ultrasound signals, so that such signals are effectively only projected outward from element 42, e.g. to one side or in a limited angular range radially from backing 40. The matching layer has acoustic impedance similar to that of the medium surrounding transducer 28. Transducer 28, as discussed, can be a single element transducer which is capable of sending and receiving ultrasound waves in a range of frequencies which are typically used in medical ultrasound procedures, such as, for example, in the range from 20 KHz to 100 MHz. Clamping rings 44 have been determined to improve efficiency and add mechanical stability to transducer 28.

Motor 32 is a microminiature motor of a small size which is suitable for containment within chamber 26 of catheter 22. Microminiature motors such as small piezoelectric motors, electromagnetic motors, or shape memory motors may be used. In one embodiment, the motor is a three-phase, coreless, brushless DC electromagnetic motor, which has few components, small size and minimal complexity. Another embodiment includes a piezoelectric motor. A piezoelectric motor is preferably of a small size, such as having a diameter in the range from 0.3 mm to 4 mm. An advantage of a piezoelectric motor compared to other motors such as electrostatic motors is that the efficiency of the piezoelectric motor is independent of size such that microminiature piezoelectric motors can exhibit a high torque-to-size ratio relative to other motors. The use of such microminiature motors can eliminate problems with torque cables and rotary transformers.

Motor 32 includes a rotatable shaft 70, for direct or indirect connection to transducer 28. In this embodiment, motor 32 is configured to run in a reciprocating motion, with shaft 70 switching between rotation in a first rotary direction (e.g. for a predetermined time or number of turns) and rotation in a second, opposite, rotary direction (e.g. for a predetermined time or number of turns). Hall sensors (not shown), optical encoders (not shown), or ultrasound, back EMF, motor saliency, or a combination of one or more of these may be used in such a reciprocating embodiment to control and/or monitor angular position of motor 32. It has been determined that hall sensors are advantageous as a feedback mechanism because of their small size and mature design. In some embodiments, the ultrasound beam or signals emitted and/or received by transducer 28 is used as a feedback mechanism to precisely assess or monitor the rotational position of motor 32 (and the ultrasound beam rotated by it) relative to the rest of device 20, ensuring proper registration of images obtained through transducer 28. A seal 34, bearing, or other structure is positioned adjacent to motor 32 and shaft 70 to provide a fluid seal between the motor and the chamber surrounding transducer 28.

Shaft 70 can be a hollow shaft with a lumen 72 extending therethrough. Shaft 70 extends through the entirety of motor 32. Shaft 70 is generally configured as a cylinder in this embodiment. Lumen 72 extends through shaft 70 and permits passage of electrical conductors, (e.g. wires or cables as noted further below), mechanical operational items (e.g. guide wires), and/or other features to pass through shaft 70, allowing transmission of electrical and/or mechanical force or energy through lumen 72 without affecting the rotation of shaft 70. Transducer 28 is operatively connected to shaft 70 so that transducer 28 rotates in response to rotation of shaft 70.

Transducer 28 is operatively coupled with shaft 70 in this embodiment so that its longitudinal axis is parallel to or coincident with the rotation axis of shaft 70. Element 42 is positioned in this embodiment so that an ultrasound beam or signals emitted from element 42 travel outward from the rotation axis. Similarly, element 42 receives an ultrasound beam or signals from directions outward of the rotation axis. Transducer 28 in one example is coupled with shaft 70 through means of an intermediate support 46. Support 46 can be hollow and defining an inner lumen in a similar manner as shaft 70. Alternatively, transducer 28 could be coupled directly to shaft 70.

A portion of chamber 26 immediately surrounding transducer 28 extending towards the application end of catheter 22 can be completely filled with a fluid or other substance having acoustic impedance similar to that of blood, such as saline, oils (e.g. mineral oil or castor oil), or mixed alcohol. The substance should minimize friction acting against transducer 28 during rotation. In this way, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image. The fluid can be added to device 20 during manufacture, or alternatively could be added prior to use. When the transducer is sealed and the coupling fluid is placed into the chamber during manufacture, long term contact with the parts necessitates a non-corrosive fluid such as mineral oil or castor oil in order to preserve the shelf life of the product. Preferably, the oil is bio-compatible, acoustically transparent, and has low viscosity. Alternatively, a fluid communication port (not shown) positioned within the catheter or through the catheter wall can allow access for adding a fluid, in which case a corrosive fluid may be used. Corrosive fluids such as water, saline, and alcohol typically have more favorable combinations of bio-compatibility, acoustic transparency and viscosity.

Device 20 is designed to pass electrical signals along a conduction pathway from transducer 28 through shaft 70. In the embodiment of FIG. 1, conductors 50, 52 are part of a conduction pathway which extends from transducer 28 through lumen 72 and which is conductively operatively coupled with the console. For example, conductor 50 as a signal channel and conductor 52 as a ground channel. Conductors 50, 52 have an application side end attached to a rotating portion of the conduction pathway and a control side end (not shown) attached to a non-rotating portion of the conduction pathway, e.g. extending to a fixed conductor in the wall of catheter 22 or to the ultrasound console. Conductors 50, 52 can conduct electrical signals while undergoing a twisting motion in response to rotational motion from shaft 70 and transducer 28, without undergoing catastrophic damage.

As one example, conductors 50, 52 can be attached at a variety of locations to transducer element 42, depending on the requirements of the particular configuration. Conductors 50, 52 can be thin wires which extend through backing 40 and/or clamping rings 44 and into lumen 72. Alternatively, conductors 50, 52 can extend from the sides of transducer 28 and sealingly enter lumen 72 through a sealed port (not shown). Alternatively, backing 40 can be conductive so that the whole backing is part of the conduction path. Similarly, the matching layer could be a conductive layer which is part of the conduction path. Conductors 50, 52 may run throughout the length of the lumen of catheter 22 from transducer 28 to the ultrasound console. Alternatively, conductors 50, 52 could extend to an intermediate coupler (not shown) or control side attachment point located within catheter 22. The control side attachment point or coupler facilitates electrical communication between conductors 50, 52 and the ultrasound console. The control side attachment point is generally fixed in a non-rotational position which is on the control side of the control side end of the drive shaft 70. However, in some examples, the control side attachment point could be positioned within the hollow drive shaft. In other examples, conductors 50, 52 could be fixed into a single cable, which could be coaxial, for example. In other examples, conductors 50, 52 could be coupled with one or more intermediate conductors (for example a rigid shaft or single cable) positioned between transducer 28 and conductors 50, 52. In this way, a conduction path is achieved in a variety of ways in which the conduction path extends through shaft 70 and includes conductors 50, 52.

During operation of device 20, a physician inserts device 20 into the body of a patient and maneuvers it to a desired location, e.g. in a particular blood vessel. Once device 20 is properly positioned in or near the area of body tissue which is to be imaged, rotary motor 32 is powered such that shaft 70 rotates. Correspondingly, transducer 28 rotates about the rotation axis. Element 42 is energized through the conduction pathway (e.g. conductor 50), which receives power from the console. Element 42 transmits an ultrasound signal substantially in an outward direction relative to shaft 70 in this embodiment, i.e. substantially perpendicular to the rotation axis.

When an ultrasound signal is transmitted, the ultrasound signal passes across wall 24 of catheter 22 until it encounters an acoustic impedance boundary (e.g. body tissue, plaque, or other material which has acoustic impedance sufficiently different from bodily fluids or other surrounding material) such that the ultrasound signal is partially reflected at the surface of the body tissue. A portion of the ultrasound signal is reflected back towards transducer 28. One or more electrical signals representing reflected ultrasound received at transducer 28 are sent from transducer 28 via the conduction pathway (e.g. conductor 50) to the ultrasound console, for imaging and display to the physician. Simultaneously or subsequently transducer 28 continues to emit further ultrasound signals and the process is repeated, continuously in certain embodiments over a desired period of time.

Transducer 28 is rotated in a reciprocating manner under the power of rotary motor 32, such that it is rotated a fixed distance in one direction and then rotated a fixed distance in the opposite direction. In the FIG. 1 example, conductors 50, 52 rotate in sync with transducer 28 and in particular embodiments become at least partially twisted around each other in one direction, untwisted, and at least partially twisted around each other in the opposite direction. The control side connection point (not shown) of the conductors 50, 52 remains stationary, which facilitates controlled twisting of the conductors as well as allowing a non-rotating coupling with the console. Conductors 50, 52 are positioned within the lumen 72 with sufficient slack to allow conductors 50, 52 to become wound without damaging either conductors 50, 52 or their connection points with transducer 28 or the control side connection point. In other examples, conductors 50, 52 could be fixed into a single cable (e.g. coaxial) which is constructed with elastic (or other) characteristics which allow some twisting of the cable without undergoing catastrophic damage to the conductors. In still other examples, conductors 50, 52 are configured to undergo a twisting reaction when attached to an intermediate conductor conductively operatively positioned between the ultrasound element and conductors 50, 52.

An alternative example of device 20 is shown in FIG. 2. The FIG. 2 example is similar to the embodiments already described and all descriptions apply also to this example except for any additional and modified features discussed in relation to the FIG. 2 example.

The FIG. 2 example includes motor 32, transducer 28, coaxial shaft 80, bias member 90, and coaxial cable 100. In this example, generally at least one conduction pathway extends from transducer 28 through shaft 80, bias member 90, and coaxial cable 100. Shaft 80 and bias member 90 provide electrical conductivity between rotatable portions of device 20 and stationary portions of device 20. In this example, the control side attachment point of the conduction paths is a connection between bias member 90 and coaxial cable 100.

Shaft 80 is a rigid shaft that includes conductors as part of the conduction pathways extending therethrough. In one example, shaft 80 is a coaxial cable having an inner conductor 82 and an outer conductor 84 (FIG. 3). Inner conductor 82 and outer conductor 84 form a portion of the conduction pathways extending from the transducer to the console. Inner conductor 82 is positioned concentrically inward of outer conductor 84 as shown in FIG. 3. Inner conductor 82 and outer conductor 84 are separated and electrically insulated by an insulating layer 86. Inner conductor 82 and outer conductor 84 extend throughout the length of shaft 80 from transducer 28 through motor 32 to at least the control side end of motor 32. In other examples, shaft 80 can be a hollow shaft having wire conductors positioned therethrough as discussed previously.

Transducer 28 is operatively connected to shaft 80 so that transducer 28 rotates in response to rotation of shaft 80. Transducer 28 is operatively coupled with shaft 80 in this embodiment so that its longitudinal axis is parallel to or coincident with the rotation axis of shaft 80. A conductor 87 is electrically operatively disposed between transducer 28 and outer conductor 84 and is capable of carrying electric signals between transducer 28 and outer conductor 84. A conductor 88 is electrically operatively disposed between transducer 28 and inner conductor 82 and is capable of carrying electric signals between transducer 28 and inner conductor 82. Conductor 88 can be positioned wholly or partially within a backing piece or plate (e.g. backing 40 above). Alternatively, conductor 88 can be routed externally to transducer 28 (e.g. along face 29) and operatively connected to inner conductor 82 yet insulated from outer conductor 84 through suitable insulating ways such as a jacketed wire. Conductors 87, 88 can be wires, insulated wires, or other suitable conductors.

Bias member 90 is positioned on the control side of motor 32. Bias member 90 is a coil or helical type spring which is positioned in a coiled manner about the rotation axis in the illustrated embodiment. Bias member 90 is connected at one of its ends to shaft 80 and at its other end to motor 32, which is fixed and allows relative rotation of shaft 80 within it (i.e. a motor stator for example). Alternatively, bias member 90 could be fixed to a surrounding wall or to another stationary part. Bias member 90 includes leading spring 92 (or bias conductor) and trailing spring 93 (or bias conductor) which are disposed to operate cooperatively as a single unit. Leading spring 92 is positioned on the application side of trailing spring 93. Leading spring 92 and trailing spring 93 are separated by an insulating layer 94. Insulating layer 94 can be glue, rubber, plastic (e.g. paralene) or other suitable material which electrically insulates leading spring 92 from trailing spring 93. In other examples, insulating layer 94 can be air or a void in the case that leading spring 92 and trailing spring 93 are not connected.

Conductors 97, 98 form a portion of the conduction pathway and are positioned to carry electric signals between shaft 80 and bias member 90. Conductor 97 is attached at one end to outer conductor 84 at a connection point which could be any point on the surface of shaft 80 where outer conductor 84 is exposed. Conductor 97 is attached at the other end to leading spring 92 near the portion of leading spring 92 which is attached to shaft 80 (not shown). Conductor 98 is attached to inner conductor 82 at an end of shaft 80 where inner conductor 82 is exposed and accessible relative to outer conductor 84. Conductor 98 is attached at the other end to trailing spring 93 near the portion of trailing spring 93 which is attached to shaft 80 (not shown). Conductors 97, 98 can be wires, insulated wires, or other suitable conductors.

Cable 100 is positioned to conductively carry electric signals from bias member 90 towards the control end of catheter 22. Coaxial cable 100 has an outer conductor portion and an inner conductor portion (not shown) which is positioned concentrically inward of the outer conductor portion and which is electrically insulated from the outer conductor portion. One of either the inner conductor portion or the outer conductor portion conductively connects with leading spring 92, and one of either the inner conductor portion or the outer conductor portion conductively connects with trailing spring 93. Alternatively, cable 100 could be a PCB cable, separate conductors, or other suitable structure for carrying electric signals.

Bias member 90 is configured to convey electric signals between rotatable shaft 80 and non-rotatable coaxial cable 100 and also to store and release mechanical energy while shaft 80 is reciprocated about the rotation axis. During operation, as shaft 80 rotates about the rotation axis under a force from motor 32 from a neutral position, bias member 90 undergoes elastic deformation while maintaining the electrical conduction pathway between conductors 97, 98 and coaxial cable 100. As bias member 90 undergoes elastic deformation, a spring force accumulates within bias member 90 (i.e. stored mechanical energy) which acts against the rotational motion of shaft 80. As shaft 80 approaches its complete rotational path in a given direction, motor 32 reduces or terminates its rotational force and shaft 80 ceases rotation. In the absence of a rotational force from motor 32 the accumulated spring force in bias member 90 causes shaft 80 to begin rotating in the opposite direction. At a certain time during operations, motor 32 re-engages shaft 80 and works in conjunction with (or subsequent to) the accumulated spring force, causing shaft 80 to continue rotating even after the stored mechanical energy in bias member 90 is expended and bias member 90 has resumed a neutral (non-deformed) position. As motor 32 again causes shaft 80 to continue rotating from the neutral position, a spring force again accumulates within bias member 90 as bias member 90 undergoes elastic deformation, and the process is repeated.

In this way, the use of bias member 90 to store and release mechanical energy allows more efficient operation of device 20. Without bias member 90, motor 32 must apply a torque force to counter rotational inertia of the drive shaft when stopping rotation and changing rotational directions. In a configuration lacking bias member 90, the inertial energy is dissipated as heat and re-imparted using energy from motor 32 during a direction change. Bias member 90 allows the rotational inertia to be stored and recovered during a direction change. When shaft 80 reciprocally rotates, energy imparted from motor 32 is stored as rotational inertia which is then used to assist halting rotation and changing the rotation direction, relieving motor 32 of the substantial burden of these tasks. For example, if bias member 90 is biased toward a 0° (or neutral position), motor 32 could be configured to oscillate between −180° and 180° so that the spring can help switch from a clockwise direction to a counterclockwise direction and also help switch from a counterclockwise direction to a clockwise direction. In this way, bias member 90 reduces the demand and performance requirements of motor 32.

Device 20 can rotate in excess of 360 degrees in some examples. In other examples, a physician selects a rotation angle using the console. Choosing a small region can limit the imaged volume but can improve frame rate and vice versa. In this way, the rotary angle could be small (e.g. 20°). For obtaining a complete slice, conical, or toroidal image, it is preferable that transducer 28 be rotated at least about 360 degrees in one direction before stopping the rotation, reversing the direction at least about 360 degrees (e.g. about 720 degrees or two rotations) in the other direction, and repeating. As noted, hall sensors monitor the rotational position of transducer 28 and provide rotational position information which is used for accurately stopping and starting the reciprocating rotational motion as well as for indexing image data for accurate visual display of body tissue.

Transducer 28 is rotated about the rotation axis such that the ultrasound beam moves in a sweeping direction which takes the form of a slice or toroidal shape. In this manner, while transducer 28 rotates about the rotation axis, element 42 is able to emit and receive ultrasound signals sufficient for the ultrasound imaging system to create a 2D image representative of the body tissue adjacent to catheter 22. According to the specifics of the procedure or the desires of the physician performing the procedure, device 20 can be moved in an axial direction within a bodily orifice such that multiple two-dimensional images are created at different locations within the bodily orifice. In this way, the two dimensional images can be processed into a three dimensional image or alternatively the physician can gain a three dimensional conceptual understanding of the physical features bodily tissue adjacent to catheter 22.

The embodiments described herein including a hollow drive shaft and reciprocating motion allows device 20 to include a directly rotating transducer element which avoids the need for use of a rotating mirror design and the disadvantages associated with such design. For example, device 20 is shorter and takes up less space than a rotating mirror design. The directly rotating transducer embodiments described herein have a deeper acoustic focal depth than a rotating mirror design. In the disclosed embodiment, ultrasound waves are generated in a generally radial direction with respect to the rotation axis (i.e. the catheter axis) as opposed to a reflector design in which ultrasound waves must travel axially (relative to the rotation axis) for several millimeters before beginning to travel in a radial direction.

Device 20 facilitates capture of an image through a viewing window which is free from unnecessary acoustic attenuation such as artifacts, obstructions, or errors within the image. For example, positioning of transducer 28 at a location which is on an application side of the rotary motor 32, conductors 50, 52, and other components ensures that wires or other echogenic materials are not positioned within or across the viewing window of transducer 28, even as transducer 28 rotates in a full 360° rotation. In this way, there are no wires or other echogenic materials which could cause artifacts within the image or block portions of the redirected ultrasound waves, which provides the physician a clear view of the entirety of the viewing window. Placing wires or other conductors 50, 52 through lumen 72 of shaft 70 also permits a reduction in the overall width of device 20, as no extra space need be provided for such conductors on the periphery of the device. As used in herein, the term "window" includes a substantially obstruction-free pathway throughout the structure of device 20 between transducer 28 and organic fluids or tissue which may be positioned external to device 20 during use.

Motor 32, which is separate from and positioned near the application end of a catheter allows a uniform angular velocity to be achieved by transducer 28. This uniform angular velocity results in an ultrasound image which is free from non-uniform rotational defects (NURD) which can otherwise be a problem with use of motors remote from the transducer that power torque cables.

Device 20 is configured to be used with existing medical devices which are designed for percutaneous, intraluminal, or interstitial procedures. For example, device 20 can be used as or with a variety of catheters for different purposes, e.g. positioned on or within an application side of a catheter, depending on the particular configuration. Parts of device 20 as previously described can be positioned within an existing lumen within the catheter. In an alternative embodiment, device 20 could include an external casing which is similar to catheter 22 having walls 24 but being shortened so as to compactly contain device 20. Device 20 could be mounted externally to a catheter using a variety of mounting devices, glues or other types of arrangements. It will be understood by those skilled in the art that the particular type of mounting procedure for device 20 to an existing medical device can include a variety of different types of mounting methods. Accordingly, the particular methods described herein are not indicative of any limiting aspects of the usage capabilities of device 20.

Other features may be included with the embodiments noted herein such as indexing systems and three-dimensional ultrasound devices.

While some of the above discussion concerned specific use in the context of ultrasound system applications, it will be understood that embodiments of device 20 could also be used for a variety of other medical procedures and with a variety of other medical devices. The versatility of the embodiments described herein allows device 20 to be used to guide percutaneous therapeutic interventions such as, for example, embolism coils, stents, filters, graphs, balloons, biopsies, and ministering therapeutics, etc. Device 20 can be used to locate various anatomical landmarks that will be used to correctly place or guided therapy. Typical landmarks include confluences, bifurcations, side branches, nearby vessels, nearby nerves, the heart, and other tissues adjacent to vessels or other orifices containing the transducer. Device 20 can also be used to locate diseased tissue that will be treated or avoided. Device 20 can be used during a biopsy to provide an image of a needle being deployed into tissue. During a TIPS (transjugular intrahepatic portocaval shunt) procedure an image can be produced to allow a physician to watch a needle being placed into the portal vein. For AAA (aortic abdominal aneurysm) graft delivery, device 20 can allow a physician to place a guide wire into a contralateral leg. Device 20 could also be used to image the location of a deployed implantable device both during and after deployment.

Although particular materials were highlighted herein for some components of device 20, those materials are not intended to be limiting of the types of materials which are suitable to be used in device 20. Additionally, where materials were not highlighted, a variety of materials could be used such as certain types of metals, polymers, ceramics or other types of materials which are suitable for use in devices for subcutaneous use as well as IVUS imaging procedures.

Device 20 could also be used for a variety of other medical procedures and with a variety of other medical devices. It will be understood by those skilled in the art that the particular type of mounting procedure can include a variety of different types of mounting methods. Accordingly, the particular methods described herein are not indicative of any limiting aspects of the usage capabilities of device 20.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by the following claims are desired to be protected. It will be understood that structures or other features described with respect to one particular embodiment or item may be used in connection or along with other features, items or embodiments included herein. All publications, patents, and patent applications cited in this specification are herein incorporated by reference as if each individual publication, patent, or patent application were specifically and individually indicated to be incorporated by reference and set forth in its entirety herein. In particular, Application Ser. Nos. 61/713,186 and filed Oct. 12, 2012; 61/713,172 and filed Oct. 12, 2012; 61/713,142 and filed Oct. 12, 2012, are each incorporated herein by reference in their entireties.

What is claimed is:

1. A medical ultrasound device, comprising:
   a stationary motor having drive shaft, wherein the drive shaft extends substantially along a rotation axis, wherein operation of the stationary motor rotates the drive shaft about the rotation axis;
   a transducer configured for transmitting and/or receiving ultrasound signals and operatively coupled with the drive shaft so that it rotates in response to rotation of the drive shaft, wherein the transducer is rotatable about the rotation axis through a range which defines a viewing window extending from the transducer;
   a first conduction path extending from the transducer through the drive shaft, wherein a portion of the first conduction path includes at least a first conductor extending through the drive shaft; and
   a bias member including at least one spring, the bias member having a first and second end, wherein the first end is fixedly attached to the drive shaft and the second end is fixedly disposed relative to the stationary motor,
   wherein the stationary motor has an operational state in which the stationary motor rotates the drive shaft about the rotation axis alternatingly between a first rotational direction and an opposite second rotational direction.

2. The device of claim 1, wherein the bias member includes a leading spring coiled around the drive shaft and a trailing spring coiled around the drive shaft.

3. The device of claim 1, wherein the first conductor is integral to the drive shaft.

4. The device of claim 3, further comprising a second conduction path extending from the transducer through the drive shaft, wherein a portion of the second conduction path includes at least a second conductor integral to the drive shaft and extending through the drive shaft, wherein the first and second conductors are fixedly attached within the drive shaft and rotate with the drive shaft.

5. The device of claim 4, wherein the drive shaft is a coaxial cable, and wherein the first conduction path is positioned concentrically relative to the second conduction path.

6. The device of claim 4, wherein each of the first and second conduction paths have respective non-rotating control side portions that are on the control side of the motor.

7. A medical ultrasound device, comprising:
a stationary motor having a drive shaft, wherein the drive shaft is positioned radially inward of the motor, wherein the drive shaft extends substantially along a rotation axis, wherein operation of the stationary motor rotates the drive shaft about the rotation axis;
a transducer configured for transmitting and/or receiving ultrasound signals and operatively coupled with the drive shaft so that it rotates in response to rotation of the drive shaft, wherein the transducer is rotatable about the rotation axis through a range which defines a viewing window extending from the transducer, wherein the entire viewing window has acoustic attenuation that allows passage of imagable ultrasound signals;
a first conduction path extending from the transducer through the drive shaft, wherein a portion of the first conduction path includes at least a first conductor extending through the drive shaft; and
a bias member including at least one spring, the bias member having a first and second end, wherein the first end is fixedly attached to the drive shaft and the second end is fixedly disposed relative to the stationary motor, wherein the stationary motor has an operational state in which the stationary motor rotates the drive shaft about the rotation axis alternatingly between a first rotational direction and an opposite second rotational direction.

8. The device of claim 1, wherein the at least one spring is a helical spring.

9. The device of claim 1, wherein the bias member includes a first bias conductor and wherein the first bias conductor is part of the first conduction path.

10. The device of claim 9, further comprising a second conduction path, wherein a portion of the second conduction path includes at least a second conductor integral to the drive shaft and extending through the drive shaft, wherein the first and second conductors are fixedly attached within the drive shaft and rotate with the drive shaft, wherein the bias member includes a second bias conductor electrically insulated from the first bias conductor, wherein the second bias conductor is part of the second conduction path.

11. The device of claim 1, wherein the drive shaft is a hollow drive shaft defining a lumen, wherein the first conductor extends through the lumen.

12. The device of claim 1, wherein in the operational state the stationary motor rotates the drive shaft at least 180 degrees in each of the first and second rotational directions.

13. The device of claim 1, wherein in the operational state the stationary motor rotates the drive shaft throughout a user-defined range in each of the first and second rotational directions.

14. The device of claim 1, further comprising a fluidly sealed chamber enclosing the transducer, the chamber being filled with a fluid, the fluid having acoustic impedance which allows imaging therethrough.

15. The device of claim 14, wherein the fluid is selected from the group consisting of saline, water, mineral oil, castor oil, and mixed alcohol.

16. The device of claim 1, wherein the transducer includes a backing coupled to an ultrasonic element, wherein the first conduction path passes through a portion of the backing.

17. The device of claim 1, wherein the orientation and rotation of the transducer defines an ultrasound field directed away from the transducer through the viewing window, and the conductors remain outside of the ultrasound field.

18. The device of claim 1, wherein the first conduction path has a rotating portion fixed with respect to the transducer and a non-rotating portion positioned on the control side of the motor.

19. The device of claim 1, wherein the stationary motor is an electromagnetic motor.

20. The device of claim 1, comprising a catheter, wherein the stationary motor and transducer are within an application side portion of the catheter.

21. The device of claim 1, wherein the transducer is positioned on the rotation axis.

* * * * *

UNITED STATES PATENT AND TRADEMARK OFFICE
CERTIFICATE OF CORRECTION

PATENT NO. : 9,980,701 B2
APPLICATION NO. : 14/051826
DATED : May 29, 2018
INVENTOR(S) : Neal E. Fearnot et al.

Page 1 of 1

It is certified that error appears in the above-identified patent and that said Letters Patent is hereby corrected as shown below:

In the Specification

Column 2, Line 37, please replace "imagable" with --imageable--

In the Claims

Column 13, Line 25, please replace "imagable" with --imageable--

Signed and Sealed this
Twenty-third Day of October, 2018

Andrei Iancu
*Director of the United States Patent and Trademark Office*